US 8,370,081 B2

(12) United States Patent
Lerche et al.

(10) Patent No.: US 8,370,081 B2
(45) Date of Patent: Feb. 5, 2013

(54) DETERMINING PARTICLE PROPERTIES BY MEANS OF SUPERIMPOSED FIELDS

(75) Inventors: Dietmar Lerche, Berlin (DE); Uwe Mertens, Berlin (DE)

(73) Assignee: L.U.M. GmbH, Berlin (DE)

( * ) Notice: Subject to any disclaimer, the term of this patent is extended or adjusted under 35 U.S.C. 154(b) by 344 days.

(21) Appl. No.: 12/598,405

(22) PCT Filed: Apr. 30, 2008

(86) PCT No.: PCT/EP2008/055335
§ 371 (c)(1),
(2), (4) Date: Apr. 2, 2010

(87) PCT Pub. No.: WO2008/132227
PCT Pub. Date: Nov. 6, 2008

(65) Prior Publication Data
US 2010/0198523 A1 Aug. 5, 2010
US 2011/0282590 A9 Nov. 17, 2011

(30) Foreign Application Priority Data

Apr. 30, 2007 (DE) .......................... 10 2007 020 646

(51) Int. Cl.
*G01N 31/00* (2006.01)
*G06F 19/00* (2006.01)
(52) U.S. Cl. ............................... 702/29; 702/38; 702/41
(58) Field of Classification Search .................... 702/18, 702/19, 22, 25, 28, 29, 30, 72, 86, 92, 127, 702/38, 41; 250/341.8; 204/547; 356/521; 436/45
See application file for complete search history.

(56) References Cited

U.S. PATENT DOCUMENTS

| 5,095,451 | A | 3/1992 | Allen |
| 5,783,826 | A | 7/1998 | Meunier |
| 6,691,057 | B2 | 2/2004 | Lerche et al. |
| 2003/0113926 | A1 | 6/2003 | Sideris |
| 2004/0211669 | A1 | 10/2004 | Cummings et al. |
| 2008/0046193 | A1* | 2/2008 | Lerche et al. .................. 702/25 |

FOREIGN PATENT DOCUMENTS

| DE | 1 013 899 B | 8/1957 |
| DE | 41 16 313 A1 | 11/1992 |
| DE | 195 42 225 A1 | 5/1997 |
| DE | 102 08 707 A1 | 1/2003 |
| EP | 0 760 092 A1 | 3/1997 |
| EP | 0 840 887 A2 | 5/1998 |
| WO | WO 95/31712 | 11/1995 |
| WO | WO 97/16713 | 5/1997 |

OTHER PUBLICATIONS

*International Search Report (PCT/ISA210) for PCT/EP2008/055335 mailed Sep. 15, 2008.
*Written Opinion (PCT/ISA 237) for PCT/EP2008/055335 mailed Sep. 15, 2008.

* cited by examiner

*Primary Examiner* — John H Le
(74) *Attorney, Agent, or Firm* — Buchanan Ingersoll & Rooney PC

(57) ABSTRACT

Modeling the gravitational field-induced or centrifugal field-induced separation of particles of a dispersion by use of one or more additional force fields that also influence the migration of the particles. A method includes detecting and measuring the modified separation behavior with the help of concentration-measuring sensors. The force acting upon the particles can be calculated from the change in velocity of the particles, and the corresponding particle properties can be calculated if the respective field intensities are known.

26 Claims, 1 Drawing Sheet

Figure 1:
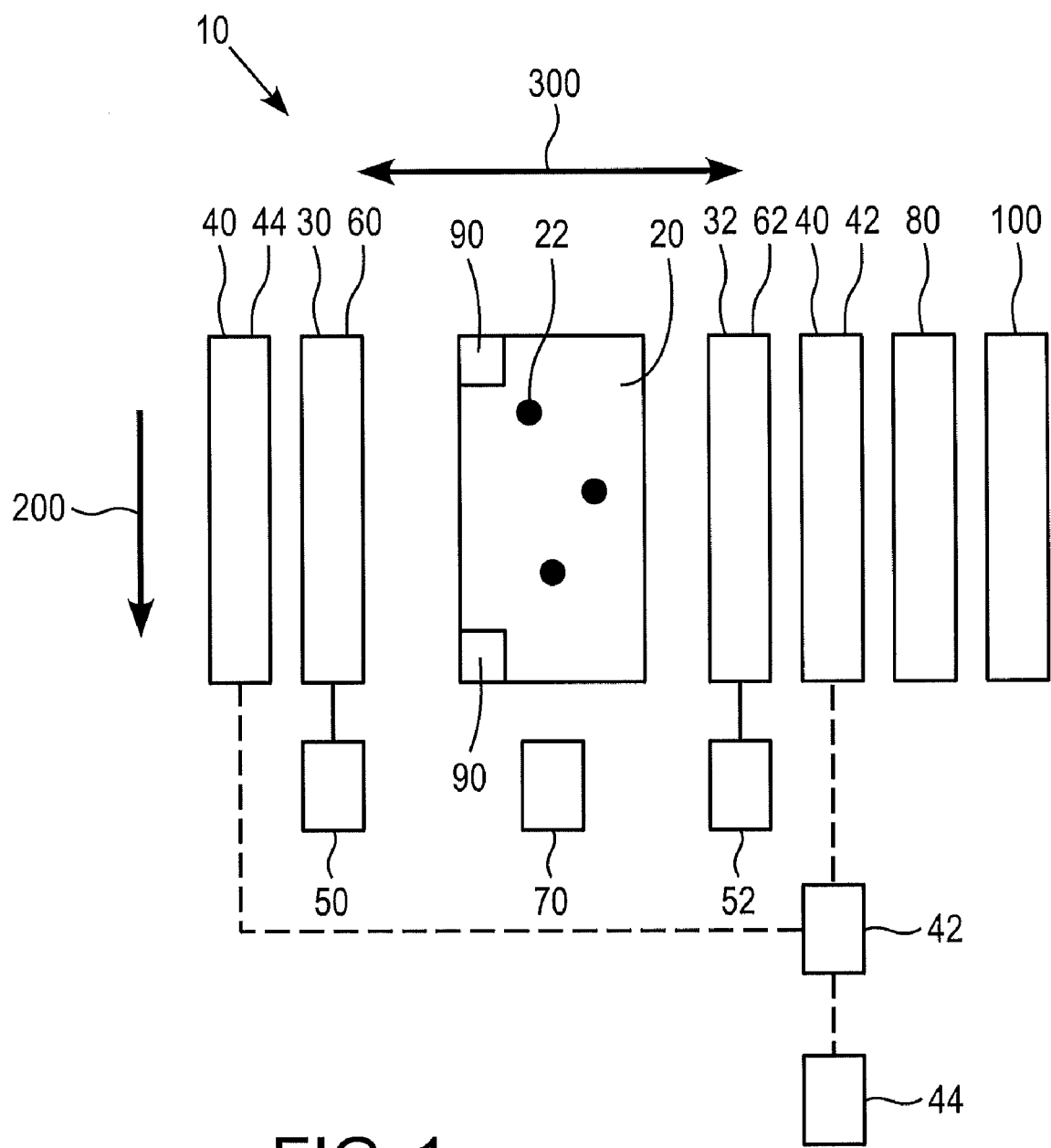

DETERMINING PARTICLE PROPERTIES BY MEANS OF SUPERIMPOSED FIELDS

BACKGROUND ART

The characterization of particles in the field of nanotechnology or biotechnology becomes more and more important in view of the constantly more complex particle structure. This concerns on the one hand product requirements (for example magnetic beads) and on the other hand realization and optimization of procedural separation processes (for example magnetic separation, electro-coagulation). In order to satisfy these new requirements, apart from size and shape of the particles electrical and magnetic particle properties have to be analyzed increasingly whereas metrological determination of the particle size is solved in principle to the point of a few nanometers (see ISO standards of TC 24) and the fundamentals of shape description and shape measurement of the particles have increasingly been worked out as well (see ISO 9276-6 F-DIS).

In particular also measuring methods are known determining the sedimentation rate or flotation rate of nanoparticles and microscale particles (see DE 41 16 313, EP 0760092, EP 0840887). By none of these methods magnetic properties of the particles can be characterized.

OBJECT OF THE INVENTION

Resulting from these fundamental technical problems it is the object of the invention to provide a method and device permitting to measure magnetic properties such as magnetizability or susceptibility of nanoparticles and microscale particles of dispersions and to indicate their distribution.

The problem is solved by exemplary aspects of a method and device described herein. Advantageous embodiments of the method and device, which are, however, not exhaustive, are the subject of additional exemplary aspects described herein.

SUMMARY

According to an exemplary aspect, disclosed is a method for characterization and determination of particle properties by the impact of superimposed fields, comprising: modeling gravitational field-induced and/or centrifugal field-induced separation of particles of a dispersion using one or more additional force fields that also influence migration of the particles; characterizing a separation behavior of the particles using concentration-measuring sensors, the behavior being modified as a function of magnitude and direction of forces operating in addition, with the characterizing performed across an entire sample length by concentration profiles resolved in time and space; and determining alteration of particle concentration as a quantity for particle properties upon which an additional force acts and/or changes of velocity vectors of the particles are determined from the concentration profiles resolved in time and space which have occurred as a function of the magnitude and direction of the forces acting in addition, from which a particle property upon which the additional force acts, is determined qualitatively and/or quantitatively.

According to an exemplary aspect, disclosed is a method wherein as additional fields homogeneous or inhomogeneous magnetic or electric fields are superimposed to the gravitational and/or centrifugation fields in any orientation, and several static field intensities are selectable and/or dynamic alterations of that forces can be realized during a measurement by means of control software.

According to an exemplary aspect, disclosed is a method comprising: measuring, in a first step, velocity distribution without additional field and after superimposition of a magnetic field acting on particle migration the velocity distribution is measured again and from alteration of mean velocity of the particles a mean magnetic force causing such reduction is calculated by means of a software module.

According to an exemplary aspect, disclosed is a method comprising: fitting measured velocity distributions before and after application of the magnetic field by a given distribution function or a free fit function, and from velocity differences of individual particle classes a magnetic force per particle class causing such modification is calculated and is represented as a distribution.

According to an exemplary aspect, disclosed is a method comprising: defining from the magnetic forces determined—if the magnetic field is known—mean particle magnetization Mp and/or its distribution across particle classes according to the following equation:

$$F_{mag} = \mu_o \cdot V_p \cdot M_p \cdot \nabla H$$

and with $M_p = \chi H$ mean susceptibility and/or its distribution is calculated or, if the magnetic flux density is known, mean susceptibility and/or its distribution is determined according to the following equation:

$$F_{mag} = 1/\mu_o \cdot \chi \cdot V_p \cdot B \cdot \nabla B.$$

According to an exemplary aspect, disclosed is a method comprising: in a first step, measuring the velocity distribution without electric field and after superimposing an electric field acting on particle migration the velocity distribution is measured again, and from the reduction of the mean velocity of the particles the mean electrical force causing such reduction for permanently charged particles or the dielectric force for particles with dipole properties is calculated by means of a software module.

According to an exemplary aspect, disclosed is a method comprising: adjusting measured velocity distributions before and after application of the electric field are adjusted by a given distribution function (for example normal distribution, log normal distribution, power distribution etc.) or a free fit function and from the velocity differences of the individual particle classes the electric force and/or dielectric force per particle class causing such modification is calculated and represented as a distribution.

According to an exemplary aspect, disclosed is a method comprising: calculating from the electrical forces determined—if the electric field is known—for charged particles according to the following equation:

$$b_e = \frac{V}{E} = \frac{Q}{6\Pi \cdot \eta \cdot r}$$

electrophoretic mobility, and/or for dipole particles in an inhomogeneous electric field according to the following equation:

$$b_d = \frac{V}{\Delta/E/^2} = \frac{V_p \cdot \varepsilon_o \cdot K_e}{4\Pi \cdot \eta \cdot r}$$

dielectric mobility.

According to an exemplary aspect, disclosed is a method, wherein the magnetic field is oriented within a centrifuge vertically to a migration direction of the particles, in state of rest of the centrifuge arrangement, and subsequently step by step a centrifugal field is applied, with dislocation of the particle arrangement through the centrifugal field being measured and from change of position relative to the centrifugal force, a deformation index is established characterizing the magnetic properties of the particles.

According to an exemplary aspect, disclosed is a method, wherein in addition to determination of the velocity of separation with and without superimposed fields this is also realized for different selectable temperatures of a sample and also temperature gradients are applied across the sample vertically to the migration direction of the particles due to the gravitational or centrifugal force.

According to an exemplary aspect, disclosed is a device for characterization and determination of particle properties, comprising: one or several appropriate sample vessels placed in a direction of a gravitational field or a centrifugal field and by further devices additional physical fields, which can be added optionally, and a direction and intensity of which is freely selectable, penetrate the sample vessel and concentration sensors are attached in such a way that—without impairing the field-induced migration of the particles—they measure particle concentration resolved in space and time and these data are processed by a microcontroller, sent to a PC, saved and evaluated online and/or offline.

According to an exemplary aspect, disclosed is a device, wherein for superimposition of the gravitational field with a magnetic field one or several mounting devices for one or several permanent magnets are integrated and formed with respect to the sample vessels such that the direction of the magnetic field can be applied in different angles relative to the gravitational field.

According to an exemplary aspect, disclosed is a device, wherein for generation of the magnetic field also a corresponding current-carrying coil or coils can be used and the field intensity of these coils can be changed dynamically by means of a control software.

According to an exemplary aspect, disclosed is a device, wherein the coil and/or coils accommodate the sample vessel inside the coil or the sample vessels are placed in the magnetic field generated by several coils.

According to an exemplary aspect, disclosed is a device, wherein for superimposition of the centrifugal field with a magnetic field on the rotor one or several mounting devices rotating simultaneously or one or several stationary mounting devices above and/or below the rotor for one or several permanent magnets are integrated and formed such that the direction of the magnetic field relative to the direction of the centrifugal force can be varied between 0° and 180°.

According to an exemplary aspect, disclosed is a device, wherein for generation of the magnetic field also a corresponding current-carrying coil or coils can be used and the a field intensity of these coils can be dynamically changed by a control software.

According to an exemplary aspect, disclosed is a device wherein the coil and/or coils accommodate the sample vessel inside the coil or the sample vessels are placed in the magnetic field generated by several coils.

According to an exemplary aspect, disclosed is a device wherein one or several sensors detect the magnetic field intensity.

According to an exemplary aspect, disclosed is a device wherein electrodes are integrated into the sample vessels for application of a stationary or dynamic electric field.

According to an exemplary aspect, disclosed is a device comprising: an arrangement and form of the electrodes for generating homogeneous or inhomogeneous fields.

According to an exemplary aspect, disclosed is a device comprising: a variable heat radiation source, which is oriented vertically to the gravitational field-induced or the centrifugal field-induced migration direction of the particles, for establishing a temperature gradient within the sample.

DETAILED DESCRIPTION

According to an exemplary aspect, disclosed is a device comprising: concentration sensors based upon electromagnetic or acoustic waves are integrated into the sample vessel or radiate through the sample vessel.

According to an exemplary aspect, disclosed is a device according to claim 22, comprising: a specification of the sensors in the form of one CCD line or several CCD lines or a CCD array oriented towards a main migration direction of the particles and monochromatic or polychromatic radiation of a test sample across an entire sample length is made by a source emitting parallel radiation or by parallelized radiation.

The invention is based upon the fundamental idea of superimposing/modeling the gravitational field-induced or centrifugal field-induced separation of particles of a dispersion by means of one or more additional force fields that also influence the migration of the particles. These additional forces will either accelerate or slow down the movement of particles. By the direction of the additional force fields and their magnitude the additional forces can be changed. Thus, in the case of monodisperse particles of equal shape and composition, sedimentation can be stopped entirely by superimposing an opposite-directed magnetic field force which magnitude is, however, equal to the magnitude of the centrifugal force. But in case having applied a constant magnetic field it is also possible to change the centrifugal force by changing the rotational speed up to equilibrium of these two forces. This second embodiment is especially simple to realize from a technical point of view.

By means of concentration-measuring sensors the modified separation behavior can now be detected and in particular the particle concentration existing at any time and in any is place can be measured, for example photometrically. From these concentration changes particle velocities can be calculated in dependence on the acting field vectors by means of the mass flow caused by it. The force acting upon the particles can be calculated from the change in velocity of the particles, and the corresponding particle properties can be calculated, if the respective field intensities are known.

As additional fields homogeneous or inhomogeneous magnetic or electric fields can be superimposed to the gravitational and/or centrifugational fields in any orientation, preferably parallel or orthoparallel. It is advantageous to be able to use several static field intensities and/or to be able to realize dynamic modifications during a measurement by means of a control software. The basic procedure is defined by a first step in which the velocity distribution is measured without additional field as a result of the gravitational field or a selectable centrifugal field, and the velocity distribution is measured again after superimposing the magnetic or electric field counteracting for example particle migration.

Already from reduction of the mean particle velocity it is possible to classify qualitatively different particles. Moreover, it is possible that this mean magnetic force causing such velocity alterations is calculated by means of a software module. More detailed analyses compare the measured velocity distributions before and after application of the magnetic field by adjusting a given distribution function (for example normal distribution, log normal distribution, power distribution etc.) or a free fit function, and calculating from the velocity differences of the individual particle classes the magnetic force per particle class causing such modification and representing it as a distribution.

From the magnetic forces determined one can define—if the magnetic field is known—the mean particle magnetization $M_p$ and/or its distribution over the particle classes according to the following equation $$F_{mag} = \mu_o \cdot V_p \cdot M_p \cdot \nabla H$$

and with $M_p = \chi H$ the mean susceptibility and/or its distribution can be calculated. If on the other hand the magnetic flux density is known, mean susceptibility and/or its distribution can be determined accordingly.

Apart from magnetic fields also homogeneous or inhomogeneous electric fields can be used. Compared to what has been said above, in a first step the velocity distribution is measured without electric field and after application of an electric field, which for example counteracts particle migration, the velocity distribution is measured again. From the reduction of the mean velocity of the particles the mean electrical force causing such reduction for permanently charged particles or the dielectric force for particles with dipole properties is calculated by means of a software module. More detailed evaluations are made in accordance with the magnetic field and approach described above for charged particles the electrophoretic mobility and/or for dipole particles in an inhomogeneous electric field the dielectric mobility.

If for example permanent magnets are located laterally in a north-south orientation to the cells taking up the dispersion of magnetic or magnetizable particles, in resting state (e.g. no centrifugation) the particles may gather between the magnetic poles (formation of a bridge). If the cell and laterally attached the magnets by means of a holder are fastened radially on a rotor and the rotational speed of the centrifuge is constantly increased, the "bridge" is deformed in radial direction. The degree of deformation and/or the rotational speed—when the "bridge" breaks—permits classification of the magnetic properties of the particles.

Surprisingly it has turned out that also due to temperature gradients, applied across the sample vertically to the migration direction of the particles, under simultaneous impact of a gravitational or centrifugal force, modifications of the separation behavior result, which are associated, for example, with the dispersibility of the particles.

As shown in FIG. 1, a device 10 for characterization and determination of the magnetic and electrical particle properties permits to place one or several appropriate holders with sample cells 20 in the direction of the gravitational field or a centrifugal field 200 and to apply by further devices additional physical fields 300, which can be added optionally, and the direction and intensity of which is freely selectable, and which penetrate the probe vessel. The concentration sensors 40 are attached in such a way that—without impairing the field-induced migration of the particles 22—they measure the particle concentration resolved in space and time. These data are processed by a microcontroller 42 realizing also the entire control of the unit and the sensors, sent to a PC (personal computer) 44, saved there and evaluated online and/or offline.

For superimposition of the gravitational field 200 with a magnetic field 300 one or several mounting devices 50, 52 for one or several permanent magnets 30, 32 are integrated and formed with respect to the sample vessels 20 such that the direction of the magnetic field can be applied in different angles relative to the gravitational field 200. It is also advantageous to use a corresponding current-carrying coil or coils 60, 62 for generation of a magnetic field, and to change dynamically the field intensity of these coils by controlling the current density by means of a control software.

For superimposition of the centrifugal field with a magnetic field on the rotor 70 one or several mounting devices rotating simultaneously or one or several stationary mounting devices 50, 52 above and/or below the rotor for one or several permanent magnets are integrated and formed such that the direction of the magnetic field relative to the direction of the centrifugal force can be varied between 0° and 180°. For generation of the magnetic field also a corresponding current-carrying coil or coils 60, 62 can be used and the field intensity of these coils can be dynamically changed by a control software. In the case of a coil and/or coils the sample vessel can be placed inside the coil or the sample vessel or sample vessels can be placed in the magnetic field generated by several coils. It is advantageous that one sensor or several sensors 80 record the magnetic field intensity.

For determination of electric parameters electrodes 90 are integrated into the sample vessels 20 for application of a stationary or dynamic electric field which can generate homogeneous or inhomogeneous fields due to the arrangement and form of the electrodes.

By the use of a variable heat radiation source 100, which is oriented vertically to the gravitational field-induced or the centrifugal field-induced migration direction of the particles, a temperature gradient can easily be realized within the sample.

The device is further characterized by the fact that concentration sensors 40 based upon electromagnetic or acoustic waves are integrated into the sample vessel or radiate through the sample vessel. A specification of the sensors is in the form of one CCD line or several CCD lines or a CCD array 42 oriented towards the main migration direction of the particles. The monochromatic or polychromatic radiation of the test sample across the entire sample length is made by means of a source 44 emitting parallel radiation or by means of parallelized radiation.

The invention claimed is:

1. A method for characterization and determination of particle properties by an impact of superimposed fields, comprising:
modeling gravitational field-induced and/or centrifugal field-induced separation of particles of a dispersion using one or more additional force fields that also influence migration of the particles;
characterizing a separation behavior of the particles using concentration-measuring sensors, the behavior being modified as a function of magnitude and direction of forces operating in addition, with the characterizing performed across an entire sample length by concentration profiles resolved in time and space; and
determining alteration of particle concentration as a quantity for particle properties upon which an additional force acts, and/or determining changes of velocity vectors of the particles from concentration profiles resolved in time and space which have occurred as a function of the magnitude and direction of the forces acting in addition, from which a particle property upon which the additional force acts, is determined qualitatively and/or quantitatively.

2. The method according to claim 1, wherein as additional fields homogeneous or inhomogeneous magnetic or electric fields are superimposed to the gravitational and/or centrifugation fields in any orientation, and several static field intensities are selectable and/or dynamic alterations of that forces can be realized during a measurement by means of control software.

3. The method according to claim 1 comprising:
measuring, in a first step, velocity distribution without additional field and after superimposition of a magnetic field acting on particle migration the velocity distribution is measured again and from alteration of mean velocity of the particles a mean magnetic force causing such reduction is calculated by means of a software module.

4. The method according to claim 3, comprising:
fitting measured velocity distributions before and after application of the magnetic field by a given distribution function or a free fit function, and from velocity differences of individual particle classes a magnetic force per particle class causing such modification is calculated and is represented as a distribution.

5. The method according to claim 3 comprising:
defining from the magnetic forces determined, if the magnetic field is known, mean particle magnetization Mp and/or its distribution across particle classes according to the following equation:

$$F_{mag} = \mu_o \cdot V_p \cdot M_p \cdot \nabla H$$

wherein $F_{mag}$ represents magnetic force, $\mu_o$ represents magnetic field constant, $V_p$ represents particle volume, $M_p$ represents mean particle magnetization, and $\nabla H$ represents magnetic field gradient,
and with $M_p = \chi H$ mean susceptibility and/or its distribution is calculated or, if the magnetic flux density is known, mean susceptibility and/or its distribution is determined according to the following equation:

$$F_{mag} = 1/\mu_o \cdot \chi \cdot V_p \cdot B \cdot \nabla B$$

wherein $F_{mag}$ represents magnetic force, $\mu_o$ represents magnetic field constant, $\chi$ represents magnetic susceptibility, $V_p$ represents particle volume, B represents magnetic flux density, and $\nabla B$ represents magnetic field gradient.

6. The method according to claim 1, comprising:
in a first step, measuring the velocity distribution without electric field and after superimposing an electric field acting on particle migration the velocity distribution is measured again, and from the reduction of the mean velocity of the particles the mean electrical force causing such reduction for permanently charged particles or the dielectric force for particles with dipole properties is calculated by means of a software module.

7. The method according to claim 6, comprising:
adjusting measured velocity distributions before and after application of the electric field are adjusted by a given distribution function or a free fit function and from the velocity differences of the individual particle classes the electric force and/or dielectric force per particle class causing such modification is calculated and represented as a distribution.

8. The method according to claim 6, comprising:
calculating from the electrical forces determined, if the electric field is known, for charged particles according to the following equation:

$$b_e = \frac{V}{E} = \frac{Q}{6\Pi \cdot \eta \cdot r}$$

electrophoretic mobility, wherein V represents voltage, E represents field strength, Q represents particle charge, $\eta$ represents viscosity, and r represents particle radius,
and/or for dipole particles in an inhomogeneous electric field according to the following equation:

$$b_d = \frac{V}{\Delta/E/^2} = \frac{V_p \cdot \varepsilon_o \cdot K_e}{4\Pi \cdot \eta \cdot r}$$

dielectric mobility,
wherein V represents voltage, E represents field strength, $V_p$ represents particle volume, $\varepsilon_o$ represents dielectric constant, $K_e$ represents complex permitivity, $\eta$ represents viscosity, and r represents particle radius.

9. The method according to claim 1, wherein the magnetic field is oriented within a centrifuge vertically to a migration direction of the particles, in state of rest of the centrifuge arrangement, and subsequently step by step a centrifugal field is applied, with dislocation of the particle arrangement through the centrifugal field being measured and from change of position relative to the centrifugal force, a deformation index is established characterizing the magnetic properties of the particles.

10. The method according to claim 1, wherein in addition to determination of the velocity of separation with and without superimposed fields this is also realized for different selectable temperatures of a sample and also temperature gradients are applied across the sample vertically to the migration direction of the particles due to the gravitational or centrifugal force.

11. A device for characterization and determination of particle properties, comprising:
one or several sample vessels containing particles, wherein the one or several sample vessels are placed in a direction of a gravitational field or a centrifugal field and at least one additional force field generated by a device, wherein the at least one additional force field is not a gravitational field or a centrifugal field, wherein the at least one additional force field influences migration of the particles and a direction and intensity of which is freely selectable, the at least one additional force field penetrating the sample vessel, and
concentration sensors attached in such a way that, without impairing the field-induced migration of the particles, particle concentration resolved in space and time is measured and the particle concentration data is processed by a microcontroller.

12. The device according to claim 11, wherein for superimposition of the gravitational field with a magnetic field one or several mounting devices for one or several permanent magnets are integrated and formed with respect to the sample vessels such that the direction of the magnetic field can be applied in different angles relative to the gravitational field.

13. The device according to claim 11, wherein for generation of the magnetic field also a corresponding current-carrying coil or coils can be used and the field intensity of these coils can be changed dynamically by means of a control software.

14. The device according to claim 13, wherein the coil and/or coils accommodate the sample vessel inside the coil or the sample vessels are placed in the magnetic field generated by several coils.

15. The device according to claim 11, wherein for superimposition of the centrifugal field with a magnetic field on the rotor one or several mounting devices rotating simultaneously or one or several stationary mounting devices above and/or below the rotor for one or several permanent magnets are integrated and formed such that the direction of the magnetic field relative to the direction of the centrifugal force can be varied between 0° and 180°.

16. The device according to claim 11, wherein for generation of the magnetic field also a corresponding current-carrying coil or coils can be used and the a field intensity of these coils can be dynamically changed by a control software.

17. The device according to claim 16, wherein the coil and/or coils accommodate the sample vessel inside the coil or the sample vessels are placed in the magnetic field generated by several coils.

18. The device according to claim 11, wherein one or several sensors detect the magnetic field intensity.

19. The device according to claim 11, wherein electrodes are integrated into the sample vessels for application of a stationary or dynamic electric field.

20. The device according to claim 11 comprising:
an arrangement and form of the electrodes for generating homogeneous or inhomogeneous fields.

21. The device according to claim 11, comprising:
a variable heat radiation source, which is oriented vertically to the gravitational field-induced or the centrifugal field-induced migration direction of the particles, for establishing a temperature gradient within the sample.

22. The device according to claim 11 comprising:
concentration sensors based upon electromagnetic or acoustic waves are integrated into the sample vessel or radiate through the sample vessel.

23. The device according to claim 22, comprising:
a specification of the sensors in the form of one CCD line or several CCD lines or a CCD array oriented towards a main migration direction of the particles and monochromatic or polychromatic radiation of a test sample across an entire sample length is made by a source emitting parallel radiation or by parallelized radiation.

24. The device according to claim 11, further comprising:
a PC capable of saving the particle concentration data and allowing for online and/or offline evaluation of the particle concentration data.

25. The device according to claim 11, wherein the at least one additional force field includes a magnetic field, and wherein the device for generating the at least one additional force field includes a plurality of magnets.

26. A method for characterization and determination of particle properties, comprising:
simultaneously applying the gravitational field or the centrifugal field, and the at least one additional force field that is not a gravitational field or a centrifugal field, using the device according to claim 11, to the particles of the one or several sample vessels.

* * * * *